United States Patent [19]
Leiner et al.

[11] Patent Number: 5,114,676
[45] Date of Patent: May 19, 1992

[54] OPTICAL SENSOR FOR DETERMINING AT LEAST ONE PARAMETER IN A LIQUID OR GASEOUS SAMPLE

[75] Inventors: Marco J. Leiner; Leonie Weiss; Otto S. Wolfbeis, all of Graz, Austria

[73] Assignee: AVL AG, Schaffhausen, Switzerland

[21] Appl. No.: 386,151

[22] Filed: Jul. 28, 1989

[30] Foreign Application Priority Data

Aug. 4, 1988 [AT] Austria .................. 1974/88

[51] Int. Cl.⁵ .............. G01N 21/00; C12M 1/40; C12M 1/34; G02B 6/02
[52] U.S. Cl. .............. 422/82.06; 422/82.07; 435/288; 435/291; 435/817; 128/634; 385/12
[58] Field of Search .............. 204/403; 422/82.06, 422/82.07, 58, 61; 435/288, 817, 291; 128/634; 350/96.29, 96.35, 96.34

[56] References Cited

U.S. PATENT DOCUMENTS

| | | | |
|---|---|---|---|
| 4,721,677 | 1/1986 | Clark, Jr. .................. | 435/288 |
| 4,849,172 | 7/1989 | Yafuso et al. .................. | 422/58 |
| 4,886,338 | 12/1989 | Yafuso et al. .................. | 128/634 |
| 4,954,318 | 9/1990 | Yafuso et al. .................. | 422/59 |

OTHER PUBLICATIONS

Webster, Medical Instrumentation, Application and Design, pp. 538-540, 1978.

*Primary Examiner*—Robert J. Hill, Jr.
*Assistant Examiner*—William Chan
*Attorney, Agent, or Firm*—Watson, Cole, Grindle & Watson

[57] ABSTRACT

In order to improve the response behavior of an optical sensor for determining at least one parameter in a liquid or gaseous sample, the sensor including a substrate which is provided with carrier particles and a fluorescent indicator immobilized thereon, the substrate is configured as a polymer film transparent to both excitation and emission radiation, and the individual carrier particles carrying the fluorescent indicator in immobilized form are bonded with only part of their surface to a thin layer of a thermoplastic material adhering to the polymer film and assume thermosetting properties after the carrier particles have been pressed in, whereas the other part of the surface of the carrier particles extend into an optically transparent hydrogel layer which covers the thermoplastic layer and in which the carrier particles are anchored mechanically. Such sensors may easily be attached to the end of an optical waveguide and may be made in any size by a simple punching operation.

13 Claims, 1 Drawing Sheet

OPTICAL SENSOR FOR DETERMINING AT LEAST ONE PARAMETER IN A LIQUID OR GASEOUS SAMPLE

BACKGROUND OF THE INVENTION

This invention relates to an optical sensor for determining one or more parameters in a liquid or gaseous sample, comprising a substrate which is provided with carrier particles and a fluorescent indicator immobilized thereon, and to a method of producing such a sensor.

DESCRIPTION OF THE PRIOR ART

In the field of optical measuring techniques, e.g., pH-measurement in liquid samples, considerable progress has been made during the past few years, since such techniques offer vital advantages over electrochemical methods, e.g., methods using a glass electrode. For example, optical pH-sensors do not require a reference cell and may be used for invasive measurements in the human body if they are combined with thin fiber-optical waveguides.

Various optical pH-sensors are known from the relevant literature. Basically, there are two kinds of sensors, i.e., sensors that are attached to the end of a lightguide as pre-fabricated elements, i.e., so-called planar sensors or fiber sensors of a first kind, and sensors that are fabricated by modifying the lightguide itself, i.e., fiber sensors of a second kind.

Although manufacture of the latter type of sensors, may be more elegant, it involves a number of technical problems, especially with regard to the reproducibility of sensor characteristics in manufacture. For this reason planar sensors are preferred for mass-production.

A typical sensor of the first kind is described in Anal. Chem. 52, 864 (1980), where a pH-sensitive material, which is placed at the end of an optical waveguide, is employed for invasive measurement of blood pH-values. The sensitive material is obtained by impregnating polystyrene beads with an indicator solution. In order to attach them to the end of the waveguide, a thin cellophane tube is slipped over the waveguide and filled with the polystyrene beads.

It is also possible to deposit an indicator directly on a membrane or on the surface of a solid substrate, such as glass. In "Sensor and Actuators" 9, 73 (1986) by H. Offenbacher et al. a method is proposed for immobilization of pH-indicators on glass which is then attached to the end of an optical waveguide.

Finally, the U.S. Pat. No. 3,904,373 describes a pH-sensor containing indicator dyes based on light absorption, which are coupled to the substrates by covalent bonds. Bonding the fluorescent indicators is achieved by means of functional triethoxisilanes. Suitable substrates are baked glass particles, etched glass and CPG powder (controlled porous glass). Sintering glass particles will lead to agglomerates of poor transparency and a small specific surface, however, whose response times to changes in the pH-level to be measured are too long. Nor is CPG powder an ideal material since it will lose its microporous structure upon sintering.

Other disadvantes of present-day optical sensors are the high amount of labor involved in their manufacture, which makes then hardly suited for mass-production. Besides, most fluorescent indicators are embedded in an ambient medium which is penetrated only slowly by the aqueous sample material.

SUMMARY OF THE INVENTION

It is an object of the invention to propose an optical sensor and a method of producing such a sensor which will permit large-scale manufacture in a simple manner, the sensor being characterized by a short response time to changes in sample parameters and a large effective surface, and the fluorescent indicator being provided in quasi-aqueous solution rather than attached to hydrophobic materials.

In the invention this object is achieved by using a polymer film, which is transparent to both excitation and emission radiation, as a support substrate and by providing that only part of the surface of the individual carrier particles carrying the fluorescent indicator in immobilized form be bonded to a thin layer of a thermoplastic material adhering to the polymer film and assuming thermosetting properties after the carrier particles have been pressed in, whereas the other part of the surface of the carrier particles extends into an optically transparent hydrogel layer which covers the adhesive layer and in which the carrier particles are anchored mechanically.

According to the invention a thin layer of a thermoplastic material is applied to an optically transparent polymer film, and carrier particles on which a fluorescent indicator has been immobilized, are evenly distributed on the adhesive layer and are partly pressed in and mechanically bonded by the application of heat and pressure, and a thin hydrogel layer is applied on top of the adhesive layer in order to cover the free upper parts of the individual carrier particles. In this way the individual carrier particles are not penetrated by a bonding agent but are pressed into an adhesive layer and fixed mechanically only. Through the hydrogel layer the fluorescent indicator immobilized on the carrier particle is accessible to the sample substances to be tested from virtually all sides.

In a preferred variant of the invention the carrier particles are configured as individual fibers, a small part of whose surface is fixed in the layer adhering to the polymer film while the larger part is held in the hydrogel layer. The use of a fibrous carrier material will make it possible that only a small part of the surface is fixed in the adhesive layer, whereas the larger part of the fibers extends into the hydrogel layer, thereby establishing a good mechanical bond between hydrogel layer and adhesive layer.

According to the invention pellets of silica gel containing an irreversibly bonded fluorescent indicator, or beads of microporous glass or polyacrylamide could also be used as carrier particles. For this purpose CPG beads or polyamide particles would be suited.

In order to obtain a particularly thin adhesive layer a further development of the invention provides that the adhesive layer be diluted with a solvent at a ratio corresponding to the desired film thickness, and that it be applied to and left to cure on the polymer film after adding a cross-linking agent, and that the carrier particles carrying the immobilized fluorescent indicator be evenly distributed on the adhesive layer, which should then be heated to a temperature at which it starts flowing upon application of a gentle pressure, and that the carrier particles be pressed into the adhesive layer until the adjacent polymer film is reached, allowing the adhesive coat to cool off and giving it time to cure at room temperature until cross-linkage is complete, and that a hydrogel layer be applied. Typical steps to be followed are:

(1) Apply a thermoplastic material including solvent and cross-linking agent at a defined thickness to a solid, transparent polymer film; allow the solvent to dry.

(2) Distribute the fibers carrying the immobilized fluorescent indicator over the thermoplastic material (they do not yet adhere).

(3) Heat the thermoplastic material to a temperature at which it starts flowing upon application of a gentle pressure.

(4) Gently press fibers into the adhesive material.

(5) Allow material to cool off (the fibers become mechanically fixed by the adhesive material).

(6) Remove any fibers that do not adhere.

(7) Allow the adhesive layer to cross-link at room temperature for 48 hours until it assumes thermosetting properties and no longer dissolves in aqueous media and does not release the fibers.

(8) Apply a hydrogel layer, the fibers acting as anchors.

Following these steps a sensor is obtained in which the diameter of the fibers or the diameter of the individual carrier particles is larger than the thickness of the layer adhering to the polymer film.

In a further step according to the invention the hydrogel layer may be covered with a layer of pigmented or dyed hydrogel in order to achieve an optical insulation, for example to shield off ambient light, scattered light or fluorescent light from the sample. For this purpose activated charcoal, iron oxide powder or titanium dioxide powder may be used.

In order to produce a pH-sensor the invention provides that a pH-sensitive fluorescent indicator be immobilized on the carrier particles. For measuring the $CO_2$ partial pressure a $CO_2$-permeable, ion-impermeable membrane to be attached on the side of the sample and a $CO_2$-sensitive fluorescent indicator may be provided. In this way the $CO_2$ partial pressure may be measured via changes in the inner pH value. The sensor may be coated with a silicone polycarbonate film.

For oxygen measurement the invention also permits the use of an $O_2$-permeable, ion-impermeable membrane covering the sample, and an $O_2$-sensitive fluorescent indicator.

Besides, it will also be possible to produce an optical enzyme sensor by immobilizing an enzyme from the group of hyrolases, oxidases and dehydrogenases on the carrier particles or in the hydrogel layer.

Special manufacturing advantages are obtained by applying the adhesive layer, the carrier particles carrying the immobilized fluorescent indicator, the hydrogel layer and, possibly, the $CO_2$- or $O_2$-permeable, ion-impermeable membrane over large areas of a polymer film, and by simultaneously punching a number of identical sensors from this film. As all materials used may be punched or cut, sensors of any shape and size can be produced in a simple way.

In a special variant of the sensor according to the invention a fibrous layer of microcrystalline cellulose fibers carrying a fluorescent indicator immobilized by covalent bonding is provided, the individual cellulose fibers having a diameter of 5-10 $\mu m$, i.e., preferably 8 $\mu m$, and a length of 50-200 $\mu m$, i.e., preferably 80 $\mu m$.

In the planar optical sensors produced in this way, which may be attached to the end of an optical fiber or bundle of fibers very easily, the polymer film has a thickness of as little as 20-500 $\mu m$, while the layer adhering to this film has a thickness of 5-10 $\mu m$, and the individual hydrogel layers 5-30 $\mu m$.

If fluorescent dyes are directly applied onto cellulose, the reaction kinetics is slower since the proton will move only slowly through the cellulose membrane as the pH-equilibrium is established between sample and sensor layer. If fibers are used, however, a larger surface area is obtained and the pH-equilibrium is established faster, since the proton can move through the hydrogel layer comparatively quickly before it arrives at the fluorescent indicator coupled to the fibers. In general, the use of fibers will result in faster reaction kinetics and lesser hysteresis effects than that of membranes, as well as good bonding due to cross-linking and mechanical anchoring of the fibers in the hydrogel layer, good long-term stability of the adhesive bond and a constant pK value of the fluorescent dye in the finished sensor.

Finally, another advantage of this type of sensor is that the optical insulation which is often required for the suppression of stray light, is an integral part of the sensor layer, whereas in other sensor types it must be attached to this layer mechanically in a separate operation.

BRIEF DESCRIPTION OF THE DRAWINGS

Following is a more detailed description of the invention as illustrated by the accompanying drawing, in which.

DETAILED DESCRIPTION OF THE PREFERRED EMBODIMENTS

Figure 1:
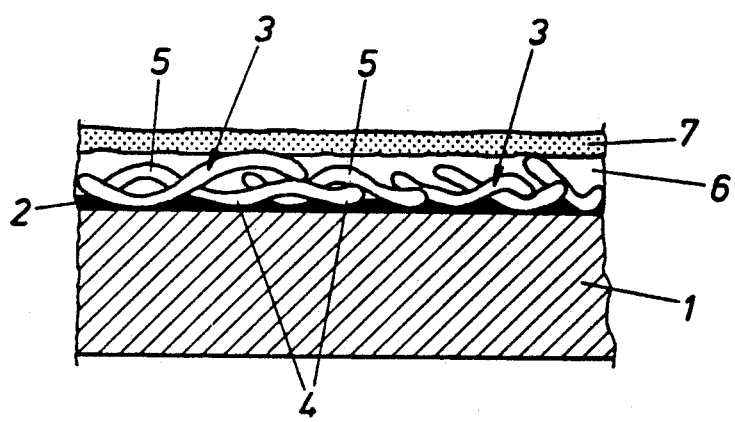
FIG. 1 presents a pH sensor according to the invention.

FIG. 1 shows a pH sensor which is provided with a polymer film 1 as a substrate, for example a mylar film, which is transparent to both excitation and emission radiation and has a thickness of 175 $\mu m$. This polymer film 1 is coated with a layer 2 of a thermoplastic material, into which the individual fibers 3 carrying the fluorescent indicator in immobilized form are pressed with part 4 of their surface and where they are held mechanically. The largest part 5 of the fibers 3 extends into hydrogel layer 6 covering the adhesive layer 2 such that the fluorescent indicator is surrounded by a quasi-aqueous medium. Suitable fluorescent indicators are 1-hydroxypyrene-3,6-8-trisulphonate, fluorescein, or a coumarin substituted in 3-position. The fibers 3 serve both as carriers for the immobilized indicator and as a mechanical anchoring means between the hydrogel layer 6 and the adhesive layer 2, the thickness of the latter being smaller than the diameters of the individual cellulose fibers.

Directly adjacent to the sample a hydrogel layer 7 is provided which is pigmented with activated charcoal, but could also be pigmented or dyed with all other substances known in this context.

Figure 2:
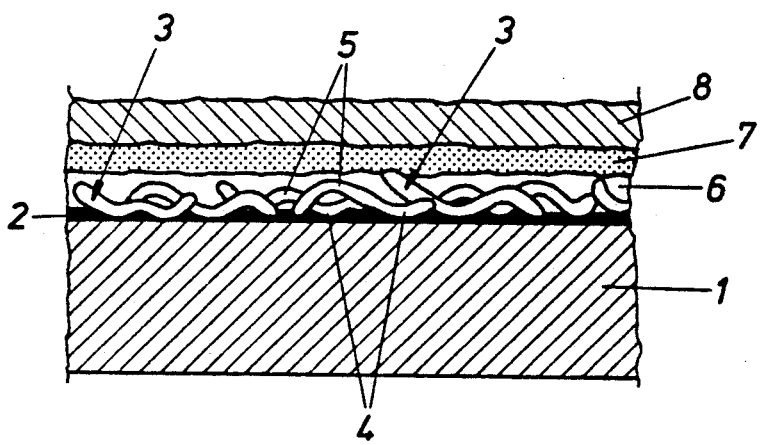
FIG. 2 presents a $CO_2$ sensor according to the invention.

The $CO_2$ sensor shown in FIG. 2, in which identical parts have identical reference numbers, is different from the pH sensor only in that it is impregnated with a phosphate or bicarbonate buffer solution of pH=8-11, which film is then covered by a $CO_2$-permeable, ion-impermeable membrane 8 on the side of the sample, for instance a silicone-polycarbonate-copolymer film of 1 mil thickness.

Figure 3:
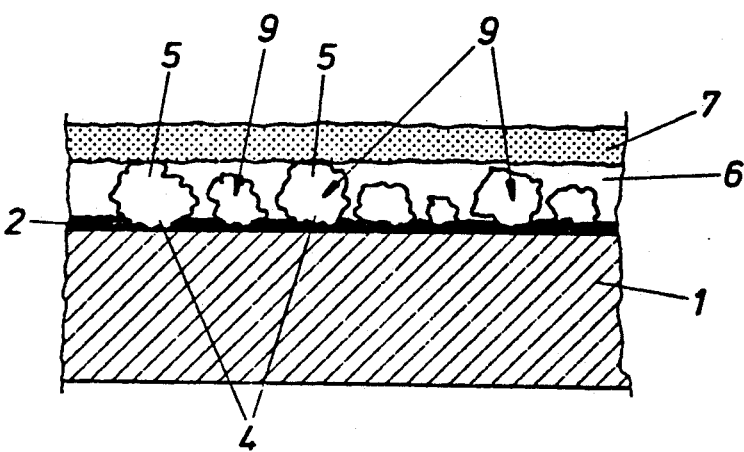
FIG. 3 presents a further variant of a planar optical sensor, each in schematic layout.

FIG. 3 presents an optical sensor in which carrier particles 9 of nonfibrous material are used. These particles may be pellets of silica gel in which a fluorescent indicator is absorbed, or microporous glass beads (CPG), or they may be made of polyamide.

We claim:

1. An optical thin-film sensor for determining at least one parameter in a liquid or gaseous sample, comprising:
   a polymer support film which is transparent to both excitation and emission radiation;
   a thin, transparent layer of a thermoplastic material adhered to said polymer film;
   an optically transparent hydrogel layer which covers said thermoplastic layer; and
   carrier particles having a diameter and a thickness with a fluorescent indicator immobilized thereon, a first part of said carrier particles being bonded to said thermoplastic material, having thermosetting properties after said carrier particles have been pressed in, and a second part of said carrier particles extending into said optically transparent hydrogel layer, said hydrogel layer being mechanically anchored by said carrier particles.

2. An optical sensor according to claim 1, wherein the diameter of the individual carrier particles is larger than the thickness of said layer adhering to said polymer film.

3. An optical sensor according to claim 1, including a layer of pigmented hydrogel covering said hydrogel layer.

4. An optical sensor according to claim 1, including a pH-sensitive fluorescent indicator immobilized on said carrier particles.

5. An optical sensor according to claim 4, including a $CO_2$-permeable, ion-impermeable membrane attached on said optical sensor for $pCO_2$ measurement.

6. An optical sensor according to claim 1, including an enzyme fromt the group consisting of hydrolases, oxidases and dehydrogenases immobilized in said hydrogel layer.

7. An optical sensor according to claim 1, wherein said carrier particles are configured as individual fibers having a surface, a small first part of the surface of said fibers is fixed in said layer adhering to said polymer film, while a larger second part of the surface of said fibers is held in said hydrogel layer.

8. An optical sensor according to claim 7, wherein a fibrous layer of microcrystalline cellulose fibers is provided, said cellulose fibers carrying a fluorescent indicator immobilized by covalent bonding.

9. An optical sensor according to claim 8, wherein said individual cellulose fibers have a diameter of 5–10 $\mu$m and a length of 50–200 $\mu$m.

10. An optical sensor according to claim 9, wherein said individual cellulose fibers have a diameter of about 8 $\mu$m and a length of about 80 $\mu$m.

11. An optical sensor according to claim 7, wherein said optically transparent hydrogel layer is covered by a layer of dyed hydrogel.

12. An optical sensor according to claim 7, including an enzyme from the group consisting of hydrolases, oxidases and dehydrogenases immobilized on said carrier particles.

13. An optical sensor according to claim 1, wherein said polymer film has a thickness of 20–500 $\mu$m, while said layer adhering to said polymer film has a thickness of 5–10 $\mu$m, and said individual hydrogel layer has a thickness of 5–30 $\mu$m.

* * * * *